(12) United States Patent
Breuer et al.

(10) Patent No.: US 10,300,082 B2
(45) Date of Patent: May 28, 2019

(54) CELL-FREE TISSUED ENGINEERED VASCULAR GRAFTS

(71) Applicant: Yale University, New Haven, CT (US)

(72) Inventors: Christopher K. Breuer, New Albany, OH (US); Tarek Fahmy, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/097,716

(22) Filed: Apr. 13, 2016

(65) Prior Publication Data

US 2016/0271152 A1 Sep. 22, 2016

Related U.S. Application Data

(62) Division of application No. 14/130,292, filed as application No. PCT/US2012/043371 on Jun. 20, 2012, now Pat. No. 9,326,951.

(60) Provisional application No. 61/501,941, filed on Jun. 28, 2011.

(51) Int. Cl.

| A61F 2/07 | (2013.01) |
| A61F 2/82 | (2013.01) |
| A61F 2/00 | (2006.01) |
| A61L 27/58 | (2006.01) |
| A61K 31/663 | (2006.01) |
| A61L 27/50 | (2006.01) |
| A61L 27/54 | (2006.01) |
| A61K 9/70 | (2006.01) |
| A61K 9/127 | (2006.01) |
| A61L 27/18 | (2006.01) |
| A61L 27/34 | (2006.01) |

(52) U.S. Cl.
CPC ............ *A61K 31/663* (2013.01); *A61K 9/127* (2013.01); *A61K 9/7023* (2013.01); *A61L 27/18* (2013.01); *A61L 27/34* (2013.01); *A61L 27/507* (2013.01); *A61L 27/54* (2013.01); *A61L 27/58* (2013.01); *A61L 2300/602* (2013.01); *A61L 2300/62* (2013.01); *A61L 2300/622* (2013.01); *A61L 2300/624* (2013.01)

(58) Field of Classification Search
CPC .. A61L 27/58; A61L 2300/41; A61L 2300/42; A61L 2300/602; A61L 2300/256; A61L 27/3625; A61L 2300/416; A61L 27/34; A61F 2/07; A61F 2/82; A61F 2210/0004; A61K 9/0024; A61K 2039/505
See application file for complete search history.

(56) References Cited

U.S. PATENT DOCUMENTS

| 2002/0187184 A1* | 12/2002 | Golomb ................. A61K 9/127 424/450 |
| 2003/0136860 A1 | 7/2003 | Hurley |
| 2004/0044405 A1 | 3/2004 | Wolff |
| 2005/0220848 A1 | 10/2005 | Bates |
| 2008/0097575 A1* | 4/2008 | Cottone ................ A61F 2/91 623/1.13 |
| 2010/0129414 A1* | 5/2010 | Dolan .................. A61K 9/127 424/423 |

FOREIGN PATENT DOCUMENTS

WO WO 2009089324 A1 * 7/2009 ............. A61L 27/18

OTHER PUBLICATIONS

Cheng, et al., "Role of macrophages in restricting herpes simplex virus type 1 growth after ocular infection", Invest Ophthalmol. Vis. Sci., 41:1402-9 (2004).
Di Lorenzo, et al., "Akt1 is critical for acute Inflammation and histamine-mediated vascular leakage", PNAS, 106:14552-7 (2009).
Espinosa-Heidmann, et al., "Macrophage depletion diminishes lesion size and severity in experimental choroidal neovascularization", Invest. Ophthalmol. Vis. Sci., 44:3586-3592 (2003).
Gragerov, et al., "Large-scale, saturating insertional mutagenesis of the mouse genome", PNAS, 104(36):14406-11 (2007).
Krauss , et al., "Multi-organ, multi-lineage engraftment by a single bone marrow-derived stem cell", Cell, 105:369-77 (2001).
Langer and Vacanti, "Tissue engineering", Science, 260:920-6 (1993).
Mirensky, et al., "Tissue-engineered vascular grafts: does cell seeding matter?", J Ped Surg., 45(6):1299-1305 (2010).
Poh, et al., "Blood vessels engineered from human cells", Lancet, 365:2122-24 (2005).
Reumaux, et al., "Priming by tumor necrosis factor-alpha of human neutrophil NADPH-oxidase activity induced by anti-proteinase-3 or anti-myeloperoxidase antibodies", J Leukoc Biol., 80:1424-33 (2006).
Rogers and Holen,, et al., "Tumour macrophages as potential targets of bisphosphonates", J Transl Med., 9:177 (2011).
Roh, et al., "Small-diameter biodegradable scaffolds for functional vascular tissue engineering in the mouse model", Biomaterials, 29:1454-63 (2008).
Roh, et al., "Tissue-engineered vascular grafts transform into mature blood vessels via an inflammation-mediated process of vascular remodeling", PNAS, 107:4669-74 (2010).

(Continued)

Primary Examiner — Tracy Liu
(74) Attorney, Agent, or Firm — Pabst Patent Group LLP

(57) ABSTRACT

A composition containing a macrophage inhibitor may be administered in an effective amount to prevent, inhibit or reduce restenosis, thrombus or aneurysm formation in implanted polymeric vascular grafts. The composition may be administered prior to vascular graft implantation, at the same time as vascular graft implantation, following vascular graft implantation, or any combination thereof. Examplary macrophage inhibitors include bisphosphonates, anti-folate drugs and antibodies, preferably in a controlled release or liposomal formulation.

8 Claims, 7 Drawing Sheets

Specification includes a Sequence Listing.

(56) References Cited

OTHER PUBLICATIONS

Solan and Niklason, "Age effects on vascular smooth muscle: an engineered tissue approach", Cell Transplant, 14(7):481-8 (2005).
Vacanti and Langer, "Tissue engineering: the design and fabrication of living replacement devices for surgical reconstruction and transplantation", Lancet, 354 Suppl 1:S132-4 (1999).
Van Rooijen and Sanders, "Liposome mediated depletion of macrophages: mechanism of action, preparation of liposomes and applications", J. Immunol. Methods, 174:83-93 (1994).

\* cited by examiner

*p=0.045, **p=0.012
ANOVA, Fischer's PLSD

*p<0.0001
ANOVA, Fischer's PLSD

SEQUENCE LISTING

<160> NUMBER OF SEQ ID NOS: 3

<210> SEQ ID NO 1
<211> LENGTH: 24
<212> TYPE: DNA
<213> ORGANISM: Artificial sequence
<220> FEATURE:
<223> OTHER INFORMATION: Synthetic primer

<400> SEQUENCE: 1
accacatgaa gcagcacgac ttct                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
tgtagttgcc gtcgtccttg aaga                                          24

<210> SEQ ID NO 3
<211> LENGTH: 25
<212> TYPE: DNA
<213> ORGANISM: Artificial Sequence
<220> FEATURE:
<223> OTHER INFORMATION: synthetic primer

<400> SEQUENCE: 3
aaggctacgt ccaggagcgc accat                                         25

CELL-FREE TISSUED ENGINEERED VASCULAR GRAFTS

CROSS-REFERENCE TO RELATED APPLICATIONS

This application is a divisional of application Ser. No. 14/130,292, which is a 371 of International Application No. PCT/US2012/043371, filed Jun. 20, 2012, which claims benefit of and priority to U.S. Provisional Application No. 61/501,941, filed Jun. 28, 2011, which is hereby incorporated herein by reference in their entirety.

STATEMENT REGARDING FEDERALLY SPONSORED RESEARCH OR DEVELOPMENT

This invention was made with government support under Agreement No. HL098228 awarded by the National Institutes of Health. The government has certain rights in the invention.

REFERENCE TO SEQUENCE LISTING

The Sequence Listing submitted Dec. 30, 2013 as a text file named "YU_5428_ST25.txt," created on Dec. 27, 2013, and having a size of 895 bytes is hereby incorporated by reference pursuant to 37 C.F.R. § 1.52(e)(5).

FIELD OF THE INVENTION

The invention is generally related to the field of vascular stenosis and restenosis, more particularly to cell-free tissue engineered vascular grafts.

BACKGROUND OF THE INVENTION

Stenosis followed by thrombosis is the major cause of synthetic vascular graft failure. Tissue engineered vascular grafts (TEVGs) offer many advantages to these synthetic grafts, but also have limitations of their own. TEVGs are typically prepared by seeding autologous cells onto a biodegradable polymeric tubular scaffold. The scaffold degrades by hydrolysis, ultimately leaving only the living vessel in the patient.

The methodology of seeding synthetic vascular grafts with autologous cells, however, is still problematic for many reasons. First, it requires an invasive procedure (biopsy) in addition to the need for a substantial period of time in order to expand the cells in culture that limited its clinical utility. This approach also faces the inherent difficulty in obtaining healthy autologous cells from diseased donors (Poh, et al., *Lancet*, 365:2122-24 (2005); Solan, et al., *Cell Transplant.*, 14(7):481-8 (2005)). The use of cell culture also results in an increased risk of contamination and even the potential for dedifferentiation of the cultured cells. The use of autologous cells to seed the polymeric grafts also limits the off-the-shelf availability of tissue engineered vascular grafts, thereby limiting their overall clinical utility. TEVGs that do not require cell seeding would offer many therapeutic, economic, and safety advantages.

It is an object of the invention to provide methods for increasing the patency of biodegradable, synthetic vascular grafts without using cell seeding.

It is a further object of the invention to provide a cell-free TEVG with improved patency and reduced graft stenosis.

SUMMARY OF THE INVENTION

The disclosed compositions and methods are based on the discovery that cell seeding of tissue engineered vascular grafts (TEVGs) inhibit stenosis by altering the recruitment of monocytes and the infiltration of macrophages in the scaffold of the TEVG. Methods for increasing the patency of biodegradable, synthetic vascular grafts by inhibiting macrophage infiltration are therefore disclosed. Cell-free TEVG produced by this method are also disclosed. The methods involve either administering a composition containing a macrophage inhibitor such as a bisphosphonate, anti-folate, or antibody either to the subject receiving the TEVG and/or to the TEVG prior to implantation.

The TEVGs do not require cell seeding, avoiding many problems associated with seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed cell-free TEVGs therefore have a greater off-the-shelf availability and increased overall clinical utility.

A composition containing a macrophage inhibitor may be administered in an effective amount to prevent, inhibit or reduce restenosis, thrombus or aneurysm formation in implanted polymeric vascular grafts. The composition may be administered prior to vascular graft implantation, at the same time as vascular graft implantation, following vascular graft implantation, or any combination thereof. In one embodiment, the composition is administered either locally or systemically from a controlled release formulation.

In a preferred embodiment, the composition is administered locally at the site of graft implantation using a controlled release formulation. In some embodiments, the composition is incorporated into or onto the polymeric vascular graft which functions as a controlled release formulation. The composition may be dispersed evenly throughout the polymeric vascular graft using any known suitable method. In another embodiment, the composition is encapsulated in a second polymeric matrix that is coated on or incorporated into the polymeric vascular graft. In some embodiments, the composition is encapsulated into microspheres, nanospheres, microparticles and/or microcapsules, and seeded into the porous vascular graft.

The cell-free TEVGs may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

BRIEF DESCRIPTION OF THE DRAWINGS

(FIG. 3C) in macrophage depleted mice after administration of 0 µl (column 1), 100 µl (column 2), or 600 µl (column 3) clodronate liposome.

DETAILED DESCRIPTION OF THE INVENTION

I. Definitions

Figure 1A:
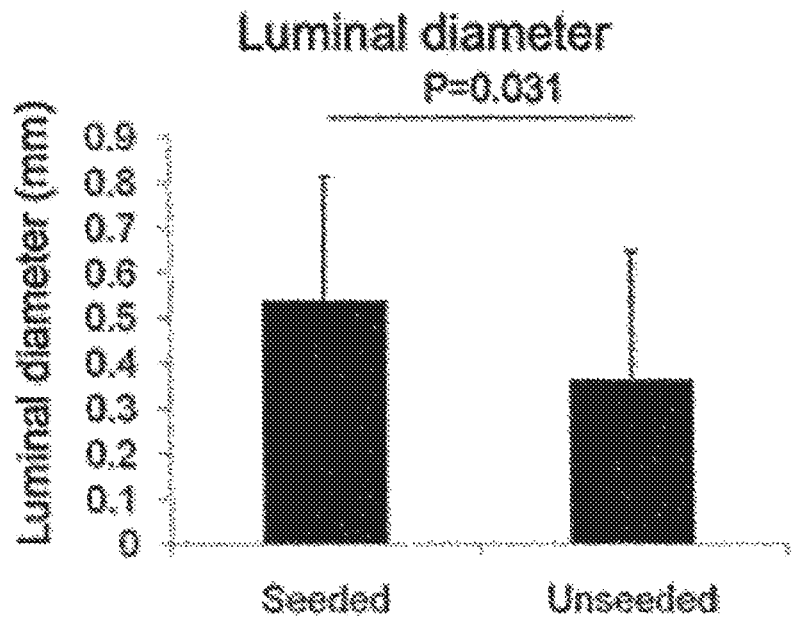
FIGS. 1A and 1B are graphs demonstrating luminal diameter (mm) (FIG. 1A) or macrophage infiltration (cell/HPF (x400)) (FIG. 1B) in a C57/B16 murine model 2 weeks after implantation of TEVG that were unseeded (bar 2) or seeded (bar 1) with syngeneic bone marrow derived mononuclear cells.

The term "vascular stenosis" refers to an abnormal narrowing in a blood vessel that occurs following an injury to the vessel wall (endothelium). In some embodiments, stenosis involves a reduction in the circumference of a lumen of 50% or more. The term "restenosis" refers to stenosis at a previously stenotic site. Restenosis, as used herein, encompasses occlusion. Exemplary injuries that result in stenosis or restenosis include trauma to an atherosclerotic lesion (as seen with angioplasty or stent), a resection of a lesion (as seen with endarterectomy), an external trauma (e.g., a cross-clamping injury), or a surgical anastomosis.

The term "neointimal stenosis" refers abnormal narrowing in a blood vessel resulting from neointimal formation.

The term "neointima" refers to a new or thickened layer of intima (inner lining) formed in a blood vessel in response to signals from injured endothelial cells.

The term "macrophage inhibitor" as used herein refers to a composition that inhibits the migration, infiltration, growth, survival, differentiation, or protein production or secretion, of a macrophage or monocyte.

The term "liposome" refers to a lipid carrier prepared by forming a lipid bilayer. The liposome is generally biocompatible and capable of passing through hydrophobic plasma membranes due to its amphiphilicity. The diameter of liposomes is generally 20-2000 nm.

The term "vascular device" refers to a medical device administered to a blood vessel during a medical procedure. The term covers devices that may damage the vascular wall and cause neointimal stenosis. The term includes vascular grafts, angioplasty balloons, and vascular stents.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector containing a gene construct in a form suitable for expression by a cell (e.g., operably linked to a transcriptional control element).

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "individual," "host," "subject," and "patient" are used interchangeably to refer to any individual who is the target of administration or treatment. The subject can be a vertebrate, for example, a mammal. Thus, the subject can be a human or veterinary patient.

The term "treat" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" does not require absolute forestalling of the condition or disease but can also include a reduction in the onset or severity of the disease or condition. Thus, if a therapy can treat a disease in a subject having symptoms of the disease, it can also prevent that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "therapeutically effective" means that the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "small molecule" refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

The term "antibodies" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "copolymer" refers to a single polymeric material that is comprised of two or more different monomers. The copolymer can be of any form, such as random, block, graft, etc. The copolymers can have any end-group, including capped or acid end groups.

The term "biocompatible" refers to a material and any metabolites or degradation products thereof that are generally non-toxic to the recipient and do not cause any significant adverse effects to the subject.

The term "biodegradable" refers to a material that will degrade or erode under physiologic conditions to smaller units or chemical species that are capable of being metabolized, eliminated, or excreted by the subject.

The term "controlled release" or "modified release" refers to a release profile in which the active agent release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

The term "bioactive agent" or "active agent" refers to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, aptamers, siRNA, nucleic acids, and combinations thereof "Bioactive agent" includes a single agent or a plurality of bioactive agents including, for example, combinations of two or more bioactive agents.

II. Cell Free Tissue Engineered Vascular Grafts

The patency of biodegradable, synthetic vascular grafts may be increased without cell seeding using a composition containing a macrophage inhibitor. Therefore, a cell-free tissue engineered vascular graft (TEVG) is disclosed that involves administering a composition containing a macrophage inhibitor to the graft or to the subject prior to or after implantation.

The disclosed biodegradable, synthetic vascular grafts do not require cell seeding to maintain patency of the grafts. This is advantageous, because it avoids problems associated with cell seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed biodegradable, synthetic vascular grafts therefore have a greater the off-the-shelf availability and increased overall clinical utility.

A. Macrophage Inhibitors

1. Bisphosphonates

Bisphosphonates (BPs), such as zoledronic acid, are antiresorptive agents approved for treatment of skeletal complication associated with metastatic breast cancer and prostate cancer. These agents act on osteoclasts, key cells in the hone microenvironment, to inhibit bone resorption. Over the past 30 years this has led to a great reduction in skeletal-related events (SRE's) in patients with advanced cancer and improved the morbidity associated with cancer-induced bone disease. Macrophages belong to the same cell lineage as osteoclasts, the major target of BPs, and are highly phagocytic cells shown to he sensitive to bisphosphonates in model studies. See Rogers, et al. *Journal of Translational Medicine* 2011, 9:177.

In some embodiments, the macrophage inhibitor is a bisphosphonate. Bisphosphonates are compounds characterized by two C-P bonds. The P-C-P structure allows a great number of possible variations, either by changing the two lateral chains on the carbon or by esterifying the phosphate groups. Bisphosphonates used in humans include alendronate, clondronate, EB-1053, etidronate, ibandronate, incadronate, neridronate, olpadronate, pamidronate, risedronate, tiludronate, YH 529, and zoledronate.

Cells of the mononuclear phagocytic lineage are especially sensitive to bisphosphonates. Both the growth and activity of these cells are decreased by bisphosphonates. In addition, bisphosphonates have been reported to depress accessory function of monocytes, inhibit the action of mitogens on mononuclear function and on the lymphoblastic response, influence the effect of antilymphocyte serum on T lymphocytes, and inhibit migratory activities of macrophages. The sensitivity of macrophages to bisphosphonates, especially to clodronate, has been made use of to selectively destroy macrophages in vivo. If bisphosphonates are administered encapsulated in liposomes, they are taken up by the macrophages and the macrophages are then destroyed within two days.

When clodronate liposomes or microparticles come into contact with macrophages and other phagocytic cells, the phagocytes recognize the liposomes as foreign particles and proceed with destroying these invading particles. The first step in this destruction is phagocytosis in which the liposomes are engulfed by the cell into an internal vesicle known as a phagosome. Lysosomes, which contain many types of destructive enzymes, including phospholipases, fuse with the phagosome forming a phagolysosome. The lysosomal membrane also contains proton pumps which will lower the internal pH of the phagolysosome. The low pH, phospholipases and other macromolecular interactions all contribute to compromising the liposomal membrane thus releasing the encapsulated clodronate. The low internal pH of the phagolysosome may contribute to the ability of the clodronate to cross the phagolysosomal membrane into the macrophage's cytosol. Once in the cytosolic medium, clodronate is mistakenly recognized as cellular pyrophosphate and used by several Class II aminoacyl-tRNA synthetases to produce a non-hydrolyzable ATP analog, adenosine 5'-($\beta$,$\gamma$-dichloromethylene) triphosphate (AppCCl 2 p). Therefore, in preferred embodiments, the macrophage inhibitor is a liposomal clondronate (dichloromethylene bisphosphonate) (e.g., CLODROSOME).

2. Antibodies

Other compounds that can be used to inhibit macrophages include antibodies such as antibodies to CD14, IB4, OKM1, OKM9, and OKM10, or fragments or conjugates thereof.

3. Anti-folate Drugs

Anti-folate drugs such as methotrexate inhibit cellular synthesis of purines, pyrimidines, to inhibit synthesis of DNA, RNA and other nucleic acids, thymidylates, and proteins, and thereby reversibly inhibits macrophage and lymphocyte function. Other inhibitors of tetrafolate synthesis could also be used, for example, trimethoprim, pyrimethamine, pemetrexed, raltitrexed, and pralatrexate.

4. Pharmaceutically Acceptable Carriers

The macrophage inhibitors may be included within the TEVG or may be administered directly to the site of implantation before, during, or after TEVG implantation. The composition containing the macrophage inhibitors may therefore also contain a pharmaceutically acceptable carrier or excipient.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The formulation is typically buffered to a pH of 3-8 for parenteral administration upon reconstitution. Suitable buffers include, but are not limited to, phosphate buffers, acetate buffers, and citrate buffers.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

Pharmaceutical formulations can be designed for immediate release, sustained release, delayed release, pulsatile release, and/or burst release of one or more macrophage inhibitors in a therapeutically effective amount. In a preferred embodiment, the formulation provides an initial burst release of a "loading dosage", followed by a sustained release to maintain the therapeutically effective dosage. This can be accomplished using a delayed and/or extended release formulation.

In preferred embodiments, the macrophage inhibitor is encapsulated in a liposome. Liposomes are artificially-prepared vesicles composed of a lipid bilayer. Liposomes are generally composed of phospholipids. The major types of liposomes are the multilamellar vesicle (MLV), the small unilamellar vesicle (SUV), and the large unilamellar vesicle (LUV).

Liposomes are spherical vesicles, composed of concentric phospholipid bilayers separated by aqueous compartments. Liposomes adhere to and create a molecular film on cellular surfaces. The lipid vesicles comprise either one or several aqueous compartments delineated by either one (unilamellar) or several (multilamellar) phospholipid bilayers. The success of liposomes in the clinic has been attributed in part to the nontoxic nature of the lipids used in their formulation. Both the lipid bilayer and the aqueous interior core of liposomes can serve the purpose of treatment. Liposomes have been well studied as carrier of toxins for enhancing their efficacy at lower doses.

The liposomes contain one or more lipids. The lipids can be neutral, anionic or cationic lipids at physiologic pH.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids. In preferred embodiments, the liposomes contain a phosphaditylcholine (PC) head group. In preferred embodiments, the liposomes also contain cholesterol In some embodiments, the formulations contain noncationic liposomes, preferably of sphingomyelin, and a pharmaceutically acceptable carrier. In a further embodiment, the liposomes include a sphingomyelin metabolite and at least one lipid. Sphingomyelin metabolites includes, for example and without limitation ceramide, sphingosine or sphingosine 1-phosphate.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N-(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), diC$_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxyethyl)-2,3-dioleoyloxy-1,4-butanediammonium iodide. In one embodiment, the cationic lipids can be 1-[2-(acyloxy)ethyl]2-alkyhalkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl) imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine), with cholesterol being most preferred. The molar ratio of a first phospholipid, such as 1,2-diacyl-glycero-3-phosphocholines, to second lipid can range from about 5:1 to about 1:1 or 3:1 to about 1:1, more preferably from about 1.5:1 to about 1:1, and most preferably, the molar ratio is about 1:1.

The liposomes typically have an aqueous core. The aqueous core can contain water or a mixture of water and alcohol. Suitable alcohols include, but are not limited to, methanol, ethanol, propanol (such as isopropanol), butanol (such as n-butanol, isobutanol, sec-butanol, tent-butanol), pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The compounds can be incorporated into polymeric microparticles that provide controlled release of the drug(s). Release of the drug(s) is controlled by diffusion of the drug(s) out of the microparticles and/or degradation of the polymeric particles by hydrolysis and/or enzymatic degradation. Polymers that are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof. Suitable polymers also include ethylcellulose and other natural or synthetic cellulose derivatives.

Alternatively, the drug(s) can be incorporated into microparticles prepared from materials which are insoluble in aqueous solution or slowly soluble in aqueous solution, but are capable of degrading by means including enzymatic degradation and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material that is normally solid at room temperature and has a melting point of from about 30 to 300° C.

It may be desirable to alter the rate of water penetration into the microparticles. Rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins that are water insoluble, such as zein, can also be used as materials for the formation of drug containing microparticles. Additionally, proteins, polysaccharides and combinations thereof that are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations that cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Drugs can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), ppolyglycolide (PGA), poly-3-hydroxybutyrate (PHB) and copolymers thereof, poly-4-hydroxybutyrate (P4HB), poly-caprolactone, cellulose, hydroxypropyl methylcellulose, ethylcellulose, as well as blends, derivatives, copolymers, and combinations thereof.

In depot formulations containing a polymeric or oligomeric carrier, the carrier and active agent can be formulated as a solution, an emulsion, or suspension. One or more weight loss agents, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or crosslinking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and/or concentration of the polymeric carrier. Examples of such systems include those described in U.S. Pat. Nos. 4,938,763, 5,480,656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

B. Polymeric Vascular Grafts

The polymeric vascular grafts are typically tubular porous conduits fabricated using biodegradable polymers. The pores in the polymeric vascular grafts allow for recruitment and integration of host cells into the graft. It is believed that recruited host cells mediate outward vascular tissue remodeling and vascular neotissue formation. Unlike synthetic vascular grafts that are currently in clinical use, the disclosed polymeric vascular grafts are biodegradable, which allows for the grafts to become replaced by forming neotissue as they degrade. Thus, the disclosed polymeric vascular grafts offer growth potential that is not possible with currently used synthetic vascular grafts.

The disclosed grafts are preferably substantially tubular in shape with a round or substantially round cross section. The tubular grafts have a lumen extending throughout the length of the graft. The grafts may be of any appropriate length and diameter that is suitable for the intended surgical use of the graft. Typically, the graft should be slightly longer than the length of artery or vein that is to be replaced.

The porous polymeric vascular grafts may be fabricated using any appropriate method, such as melt processing, solvent processing, leaching, foaming, extrusion, injection molding, compression molding, blow molding, spray drying, extrusion coating, and spinning of fibers with subsequent processing into woven or non-woven constructs. Pores in the graft may be derived by any suitable method, including salt leaching, sublimation, solvent evaporation, spray drying, foaming, processing of the materials into fibers and subsequent processing into woven or non-woven devices. Preferably, the pores of the device are between 5 μm and 500 μm, more preferably between 5 μm and 250 μm, more preferably between 5 μm and 100 μm, in diameter.

In some embodiments, the grafts are formed from a felt or sheet like material of the polymer that can be formed into a tubular conduit. For example the device could be fabricated as a nonwoven, woven or knitted structure from extruded polymeric fibers. The polymeric sheet may be formed using any textile construction, including, but not limited to, weaves, knits, braids or filament windings. Any suitable method, such as electrospinning, may be used to fabricate the nonwoven or woven polymeric textile.

The polymers and fabrication methods selected to fabricate the polymeric vascular grafts are suitable to produce grafts with biomechanical properties suitable for use as vascular conduits. Biomechanical properties that are important for vascular graft function include initial burst pressure, suture retention strength and elasticity. In some embodiments, the initial burst pressure of the polymeric vascular graft is between about 1,500 mmHg and about 4,500 mmHg, preferably between about 2,000 mmHg and about 4,500 mmHg. In another embodiment, the polymeric vascular grafts possess suture retention strengths between about 1 N and about 5 N, preferably between about 2 N and about 4 N. In another embodiment, the intrinsic elasticity of the vascular grafts is between about 10 MPa and about 50 MPa, preferably between about 15 MPa and about 40 MPa. In another embodiment, the initial tensile strength of the vascular grafts is between about 1 MPa and about 10 MPa, preferably between about 3 MPa and about 6 MPa.

1. Biodegradable Polymers

The biodegradable, synthetic vascular grafts may be fabricated using any known biodegradable polymer, co-polymer, or mixture thereof. Many suitable biodegradable polymers are known in art.

Examples of preferred biodegradable polymers include synthetic polymers that degrade by hydrolysis such as poly(hydroxy acids), such as polymers and copolymers of lactic acid and glycolic acid, polyanhydrides, poly(ortho) esters, polyesters, polyurethanes, poly(butic acid), poly(valeric acid), poly(caprolactone), poly(hydroxyalkanoates), and poly(lactide-co-caprolactone). The foregoing materials may be used alone, as physical mixtures (blends), or as co-polymers. In a preferred embodiment, the biodegradable, synthetic vascular grafts are fabricated from polyglycolic acid or poly-L-lactic acid.

2. Sealants

Synthetic vascular grafts fabricated from nonwoven, woven or knitted sheets or felts of biodegradable polymers may be further treated with polymeric sealants. The polymeric sealants function to modify the biomechanical properties of the vascular grafts, such as tensile strength and elasticity. Polymeric sealants may also be used to control the total porosity and pore size distribution range of the vascular graft.

Polymeric sealants for the disclosed biodegradable synthetic vascular grafts may be any biodegradable polymer, including, but not limited to, the list of biodegradable polymers listed above. In one embodiment, the polymeric sealant is a copolymer of poly(ε-caprolactone) and poly(L-lactide). The copolymer can be at a ratio from 5:95 to 95:5, preferably from 30:70 to 70:30, more preferably from 40:60 to 60:40, most preferably about 50:50.

Polymeric sealants may be added to tubular synthetic grafts dissolved in an appropriate solvent to allow for the sealant to penetrate the nonwoven, woven or knitted sheet or felt of biodegradable polymers forming the graft. The polymeric sealant may then be quickly transformed from liquid to solid phase by lowering the temperature of the graft. Solvents may then be removed by an appropriate technique, such as lyophilization.

C. Additional Bioactive Agents

Additional bioactive agents that promote vascular graft adaptation may also be administered. Suitable bioactive agents or drugs include, but are not limited to: anti-thrombogenic agents, such as heparin, heparin derivatives, urokinase, and PPack (dextrophenylalanine proline arginine chloromethylketone; anti-proliferative agents, such as enoxaprin, angiopeptin, hirudin, acetylsalicylic acid, paclitaxel, 5-fluorouracil, cisplatin, vinblastine, vincristine, epothilones, endostatin, angiostatin and thymidine kinase inhibitors; anesthetic agents, such as lidocaine, bupivacaine, and ropivacaine; anti-coagulants, such as D-Phe-Pro-Arg chloromethyl keton, RGD peptide-containing compounds, heparin, antithrombin compounds, platelet receptor antagonists, anti-thrombin antibodies, anti-platelet receptor antibodies, aspirin, prostaglandin inhibitors, platelet inhibitors and tick antiplatelet peptides; cholesterol-lowering agents; vasodilating agents; and agents which interfere with endogenous vascoactive mechanisms.

III. Uses for Biodegradable, Synthetic Vascular Grafts

The biodegradable, synthetic vascular grafts may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

Vascular bypass grafting is most commonly performed for the treatment of vessel stenosis. However, vascular grafts are also used for the treatment of other conditions such as arterial aneurysm or chronic renal failure (as access for hemodialysis). Vascular grafting can be performed by conventional surgery or endovascular techniques.

Coronary artery bypass grafting (CABG) is one example of vascular bypass surgery. With this procedure, a bypass graft is used to bypass the coronary artery distal to the site of stenosis or occlusion. When a vein graft is used, one end is anastomosed to the aorta and the other end is anastomosed to the coronary artery beyond the stenosis or occlusion. When an arterial graft is used, the proximal end is left undisturbed (thus preserving the artery's normal blood inflow) and the distal end is anastomosed to the coronary artery beyond the stenosis or occlusion.

Typically, an anastomosis (i.e., the surgical union of tubular parts) between the in situ artery or vein and the synthetic graft is created by sewing the graft to the in situ vessel with suture. Commonly used suture materials include proline (extruded polypropyline) and ePTFE.

A. Method of Preventing Stenosis in TEVG

A method for promoting patency of a biodegradable, synthetic vascular graft is disclosed that involves administering a composition containing a macrophage inhibitor to the graft or to the subject prior to or after implantation.

1. Administration

Pharmaceutical compositions containing macrophage inhibitors may be administered to a subject in a number of ways before, during, or after TEVG implantation. The compositions are preferably administered parenterally (e.g., intravenously) or topically to the transplantation site before, during, or after TEVG implantation.

In other embodiments, the composition containing macrophage inhibitors is applied to the TEVG prior to implantation, preferably in liposomes or microparticles, preferably directly applied to the outer surface of the graft after implantation. The macrophage inhibitor such as clodronate may be encapsulated, for example, in microspheres, and attached to the scaffolding. This can be physically attached or incorporated or entrapped therein, or attached using a fibrin glue or alginate gelled by addition of calcium chloride.

B. Dosage

The exact amount of the compositions required will vary from subject to subject, depending on the species, age, weight and general condition of the subject, the size and location of the TEVG being implanted, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to promote TEVG patency while preventing stenosis. The dosage should not be so large as to cause adverse side effects, such as unwanted cross-reactions, anaphylactic reactions, and the like. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

In one embodiment, macrophage inhibitor is administered in a dose equivalent to parenteral administration of about 0.1 ng to about 100 g per kg of body weight, about 10 ng to about 50 g per kg of body weight, about 100 ng to about 1 g per kg of body weight, from about 1μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of macrophage inhibitor administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Although the macrophage inhibitor may be administered once or several times a day, and the duration of the treatment may be once per day for a period of about 1, 2, 3, 4, 5, 6, 7 days or more, it is more preferable to administer either a single dose in the form of an individual dosage unit or several smaller dosage units or by multiple administration of subdivided dosages at certain intervals. For instance, a dosage unit can be administered from about 0 hours to about 1 hr, about 1 hr to about 24 hr, about 1 to about 72 hours, about 1 to about 120 hours, or about 24 hours to at least about 120 hours. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours. Subsequent dosage units can be administered any time following the initial administration such that a therapeutic effect is achieved. The therapy with macrophage inhibitor can instead include a multi-level dosing regimen wherein the macrophage inhibitor is administered during two or more time periods, preferably having a combined duration of about 12 hours to about 7 days, including, 1, 2, 3, 4, or 5 days or about 15, 15, 30, 35, 40, 45, 50, 55, 60, 65, 70, 75, 80, 85, 90, 95, 100, 105, 110, 115, 120, 125, 130, 135, 140, or 144 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours.

EXAMPLES

Example 1

Murine Model of Neovessel Formation

A method for constructing small diameter biodegradable synthetic scaffolds were previously developed that are suitable for use as vascular grafts in mice (Roh, J. D., et al. Biomaterials 29:1454-1463 (2008)). These tubular scaffolds are composed of the same materials and design used in clinical TEVG, thus maintaining similar structural, mechanical, and degradation properties.

In this study, the natural history of TEVG function and neovessel formation was evaluated in the murine model. A total of 85 TEVG were implanted and harvested over the six-month time course. The results of implanting the TEVG created by seeding the scaffold with syngeneic bone marrow derived mononuclear cells as IVC interposition grafts was evaluated in CB57/BL6 mice over a six-month course.

Most graft failure resulted from stenosis, which occurred by the second week after implantation. The CB57/BL6 murine model faithfully recapitulates the results obtained in a clinical trial including similar patency and stenosis rates but over a shorter time course (Table 1).

TABLE 1

|  | Human Trial | | Mouse |
| --- | --- | --- | --- |
|  | 1 year (n = 25) | 5.8 years (n = 25) | 2 weeks (n = 25) |
| Critical Stenosis | 0 | 4 (16%) | 6 (24%) |
| Thrombosis | 0 | 1 (4%) | 0 |
| Aneurysm | 0 | 0 | 0 |
| Infection | 0 | 0 | 0 |
| Other | 0 | 0 | 0 |

It was demonstrated that implantation of the TEVG, which was created by seeding bone marrow-derived mononuclear cells onto the biodegradable tubular scaffold fabricated from polyglycolic acid fiber tube and coated with a 50:50 copolymer of polycaprolactone and polylactic acid, resulted in the formation of a neovessel. Three-dimensional computer tomography angiography of the tissue engineered vascular graft performed six-months after implantation demonstrated a widely patent vascular graft without evidence of stenosis, aneurismal dilation or thrombosis. Histological characterization of the neovessel demonstrated a laminated structure, which resembles a native vessel including formation of a neointima, neomedia, and neoadventitia. The natural history of neovessel formation involves infiltration of monocytes into the scaffold followed by formation of a monolayer of endothelial cells surrounded by concentric layers of smooth muscle cells which formed on the inner surface of the scaffold and formation of the neoadventitia within the scaffold wall.

Example 2

Role of Cell Seeding in Neovessel Formation

Materials and Methods

CB57/Bl6 IVC interposition Model: Scaffolds were constructed from a nonwoven polyglycolic acid (PGA) mesh (ConcordiaFibers) and a co-polymer sealant solution of poly-L-lactide and -ε-caprolactone (P(CL/LA)) using previously described methods (Roh, J. D., et al. Biomaterials 29:1454-1463 (2008)). Bone marrow was collected from the femurs of syngeneic CB57/BL6 mice (Jackson Laboratories; Bar Harbor, Me.). Following purification of the mononuclear cell component using Histopaque-1086 (Sigma; Saint Louis, Mo.) centrifugation, one million mononuclear cells were manually pipetted onto the scaffold. The seeded scaffold was incubated in Dulbecco's Modified Eagle's Medium (Gibco; North Andover, Mass.) overnight prior to implantation. TEVG implantations in the mice were performed as previously described (Roh, J. D., et al. Biomaterials 29:1454-1463 (2008)). All scaffolds were sutured into the infrarenal IVC of 3-4 month old, female CB57/BL6 mice (Jackson Laboratories; Bar Harbor, Me.). A total of 220 animals were implanted with either BM-MNC-seeded, unseeded, or MCP-1 eluting scaffolds. At 1 d (N), 3 d (N), 1 wk (N), 3 wk(N), 6 wk(N), 10 wk(N), and 24 wk(N), animals were sacrificed and grafts were explanted for further analysis. All animal experiments were done in accordance with the institutional guidelines for the use and care of animals, and the institutional review board approved the experimental procedures described.

Ultrasonography: Serial ultrasonography (Vevo® Visualsonics 770) was utilized for graft surveillance of the TEVG. Prior to ultrasonography, mice were anesthetized with 1.5% inhaled isoflurane. Graft luminal diameter was determined sonographically at the indicated time points after postimplantation.

Micro-computed tomography angiography (microCTA): In vivo patency and morphology of the TEVG were evaluated using microCTA. Mice were positioned in supine position and placed on animal bed of microCT scanner (eXplore CT120, GE Healthcare, USA). All animals were imaged using standard microCT imaging protocol (220 views, 16 ms X-ray exposure time, penetration energy: 70 kV/32 mA). Omnipaque contrast (GE Healthcare, USA) was utilized as a contrast agent. MicroCT images were reconstructed and visualized with MicroView (GE Healthcare, USA) and Amide (amide.sfnet) software packages to assess graft patency and vessel lumen size.

Histology: Explanted grafts were pressure fixed in 10% formalin overnight and then embedded in paraffin or glycolmethacrylate using previously published methods (Roh, J. D., et al. Biomaterials 29:1454-1463 (2008); Roh, J.D., et al. Proc. Natl. Acad. 107:4669-74 (2010)). Sections were stained with H&E.

Immunohistochemistry: Primary antibodies included rat-anti-mouse Mac-3 (BD Bioscience), F4/80 (AbD Serotec), mouse-anti-human calponin (Dako), and rabbit-anti-human vWF (Dako). Antibody binding was detected using appropriate biotinylated secondary antibodies, followed by binding of streptavidin-HRP and color development with 3,3-diaminobenzidine (Vector). Nuclei were then counterstained with hematoxylin. For immunofluorescence detection, a goat-anti-rabbit IgG-Alexa Fluor 568 (Invitrogen) or a goat-anti-mouse IgG-Alexa Fluor 488 (Invitrogen) was used with subsequent 4',6-diamidino-2-phenylindole nuclear counterstaining.

Quantitative cellularity analysis: Mouse monocytes, identified by positive F4/80 expression, were measured for each explanted scaffold. Two separate sections of each explant were counterstained with hematoxylin and imaged at 400× magnification. The number of nuclei was then counted in five regions of each section and averaged.

Morphometry of TEVG: TEVG were pressure fixed and explanted. The grafts were subsequently paraffin embedded and mounted for histologic and immunohistochemical evaluation. H&E (Sigma, St Louis, Mo.) staining was conducted to evaluate graft morphometry. Graft luminal diameter were measured using Image J software (Image Processing and Analysis in Java; National Institutes of Health, Bethesda, Md.). Stenosis was defined as greater than 50% decrease in luminal diameter. Critical stenosis was defined as 80% narrowing of the luminal diameter. Graft occlusion was defined ads 100% narrowing of the luminal diameter.

BMT: After myeloablation with 900cGy total body irradiation using a 137 Cs source, 6-week old female wild-type C57BL6 mice received a tail vein injection of $5 \times 10^6$ unfractionated nucleated bone marrow cells harvested from age and gender mismatched (male) GFP transgenic mice, as previously described (Di Lorenzo, A., et al. Proc. Natl. Acad. Sci. 106:14552-7 (2009)). Following bone marrow transplantation, the mice received antibiotics and autoclaved food and water for one month, after which they received routine daily care. Engraftment of the bone marrow was confirmed one month after bone marrow transplantation by determining the number and percentage of GFP (+) cells on a peripheral blood sample using FACS. Subsequently, one group received seeded TEVG (N=) and the second group received unseeded TEVG (N=). Specimens were explanted on post-operative day 3, 7, 14, 10 weeks and 6 months.

Composite graft: The vena cava was harvested from a male C57/Bl6 mouse. One-millimeter sections of the vena cava was anastomosed to the distal end of a scaffold. The composite scaffold was then seeded and incubated as described above. The composite TEVG was implanted in a femalenC57/B16 host (N=). Specimen were harvested on post-operative day 7, 14, at 10 weeks and 6 months.

Fluorescent in situ Hybridization (FISH): Primer pairs were synthesized as previously described (Krauss D. S., et al. Cell 105:369-77 (2001)). Slides were heated to 60° C. for 2 min, deparaffinized in Citrisolv (Fisher Scientific, Fairlawn, N.J.), and rehydrated through graded alcohols to phosphate buffered saline (PBS). Antigen retrieval was performed using sodium citrate buffer in steam for 15 min. Digoxigenin-labeled mouse Y chromosome probe was applied as described, and detected using a Rhodamine-conjugated secondary antibody to digoxigenin (Roche Diagnostics, Mannheim, Germany). Counting of Y-positive nuclei was accomplished by systematically examining the FISH-stained tissue, field by field, under 40× magnification, using a Zeiss Axiovert 200M Fluorescence/Live cell Imaging Microscope (Carl Zeiss Imaging Solutions, Thornwood, N.Y.). Digital images were acquired using the Zeiss LSM510 computer system (Carl Zeiss Imaging Solutions, Thornwood, N.Y.). Images were pseudocolored using image processing software (Adobe Photoshop, San Jose, Calif.). Cell counts were obtained by first counting all of the Y chromosome-positive cells in a defined area on the tissue, and then counting the total number of cells in that area using the immunostained photographs.

Detection of DNA in TEVG: Standard Curve Generation: DNA, for use in generating a standard curve, was isolated from 5×10⁶ GFP -positive Bone Marrow-Derived Mononuclear Cells (BM-MNCs) obtained from C57/BL6 GFP positive mice using DNeasy Blood and Tissue Kit (QIAGEN, Inc, Valencia, Calif., USA) following manufacturer's instructions. DNA concentrations were determined using NanoDrop ND-1000 (NanoDrop, Wilmington, Del., USA). Using the molecular weight of the mouse genome at $4 \times 10^{12}$ grams/mol (Gragerov et al., 2007) the DNA concentration with the units genomes/µl was determined. 10-fold serial dilutions were performed yielding concentrations of 20,000 genomes/µl to 0.2 genome/µl. These dilutions were subsequently used as qPCR standards by adding 5 µl of each concentration to each reaction resulting in a standard curve from $1 \times 10^5$ genomes to 1 genome run in triplicate.

Sample Preparation and DNA Isolation: Explanted tissue grafts were incubated overnight in 180 µl of lysis buffer (QIAGEN) and proteinase K (12 mAu/reaction) at 56° C. Following tissue digestion, DNA was isolated from samples using DNeasy Blood and Tissue Kit (QIAGEN) following manufacturer's instructions. DNA concentrations in ng/µl were determined using NanoDrop ND-1000 (NanoDrop) and converted to genomes/µl as previously described.

qPCR: The following primers and TaqMan probe were designed to amplify a specific 93 by region of the GFP gene:
  forward, 5'-ACCACATGAAGCAGCACGACTTCT-3' (SEQ ID NO:1);
  reverse, 5'-TGTAGTTGCCGTCGTCCTTGAAGA-3' (SEQ ID NO:2);
  probe, 5'-AAGGCTACGTCCAGGAGCGCACCAT-3' (SEQ ID NO:3). The TaqMan probe was labeled at the 5' end with 6-carboxyfluorescein (FAM) and a 3' end with TAMRA quencher (Applied Biosystems, Foster City, Calif., USA). qPCR was carried out with a final volume of 20 µl containing 10 µl of TaqMan Universal PCR Master Mix-UDG (Applied Biosystems), 0.33 uL (15.3 uM) of forward and 0.396 uL (12.6 uM) reverse primer, 0.5 uL (10.0 µM) of the TaqMan probe, up to 5 uL of DNA and 3.774 µL of ddH$_2$O. 6000 mouse genomes per sample were added to each reaction. For consistency, ddH$_2$O was added to each reaction to bring the final DNA template volume to 5 µL. Negative controls (containing all reagents except target DNA) along with 10-fold serial dilutions of positive control DNA were included in each run. Additionally, explanted inferior vena cava from a non-GFP mouse along with an unseeded vascular graft implanted for 3 days in a non-GFP mouse were used as negative controls. DNA amplification and quantification was performed using iCycler iQ Real-Time PCR Detection System (Bio-Rad, Hercules, Calif., USA). Each qPCR reaction consisted of the following steps: 2 min UNG incubation at 50° C. to remove possible amplicon contamination, followed by 10 min at 95° C. to activate the polymerase, and 40 cycles of 15 sec denaturing at 95° C. and 1 min at 60° C. of extension and annealing. Data were collected at the end of each elongation step and analyzed with iCycler iQ Real Time Dectection System Software (Bio-rad).

Macrophage depletion with clodronate liposomes: Depletion of macrophages in vivo was achieved with dichloromethylene diphosphonate-liposome (CL2MDP-lip) as previously described (Rooijen, N.V. & Sanders, A. J. Immunol. Methods 174:83-93 (1994); Espinosa-Heidmann, D. G., et al. Invest. Ophthalmol. Vis. Sci. 44:3586-3592 (2003); Cheng, H., et al. Ophthalmol. Vis. Sci. 41:1402-1409 (2004)). Clodronate (Roche Diagnostics, Mannheim, Germany) was encapsulated in liposomes (Reumaux, D., et al. J. Leukocyte Biol. 80:1424-1433 (2006)). Briefly, phosphatidylcholine (Lipoid, Ludwigshafen, Germany) and cholesterol (Sigma Chemical, St. Louis, Mo.) were dissolved in a mixture of methanol and chloroform. The lipids were mixed with clodronic acid dissolved in PBS. Resuspension of liposomes was achieved by water sonication at room temperature, and resultant liposomes were washed in an ultracentrifuge. Systemic macrophage depletion was achieved by CL2MDP-lip (200 ul=1 mg) via i.v. administration at 3 days and 24 hours before graft implantation and then at every 3 days after graft implantation for 2 week. Control groups received i.v. subconjunctival administration of PBS liposomes. Flow cytometric analysis was performed to evaluate the efficacy of systemic macrophage depletion. Briefly, white blood cells were separated from EDTA-anticoagulated whole blood using lysis buffer (BD bioscience, San Jose, Calif.). The white blood cells were labeled with a rat anti-mouse CD115 antigen- PE conjugate (eBioscience, San Diego, Calif.). Local depletion of macrophages on the graft was evaluated by counting F4/80 cells under ×400 high-power field.

Statistical analysis: Statistical differences were measured using a Student's t-test or analysis of variance (ANOVA). P values less than 0.05 were considered statistically significant.

Results

Figure 1B:
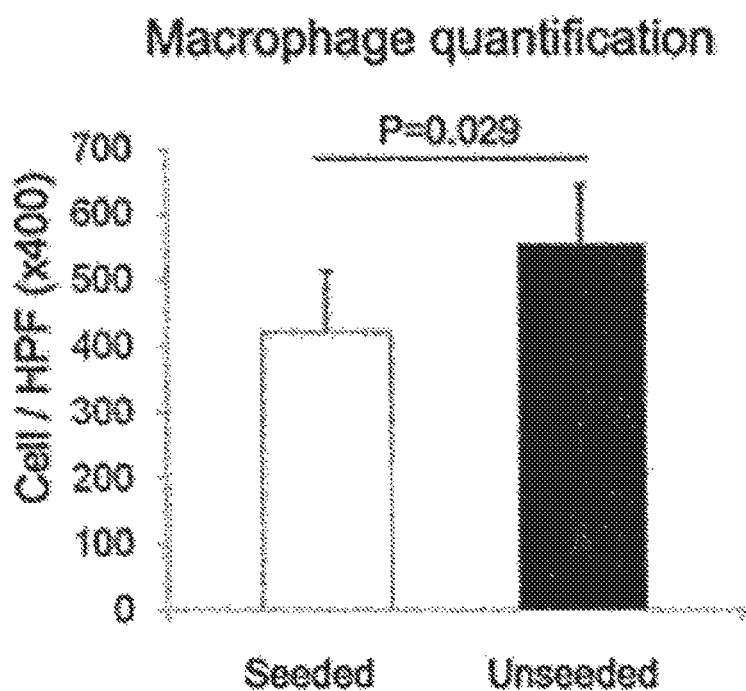
Figure 1C:
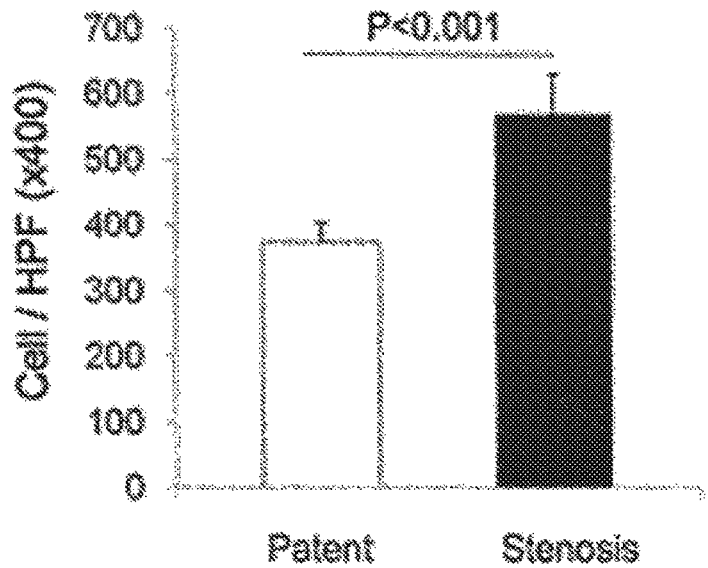
FIG. 1C is a graph showing the degree of marcrophage infiltration (cell/HPF (x400)) in patent (bar 1) and stenotic (bar 2) TEVG.

To determine the role of cell seeding on neovessel formation either unseeded scaffolds (N=25) or scaffolds seeded with syngeneic bone marrow derived mononuclear cells (N=25) were implanted as IVC interposition grafts in CB57BL6 mice and harvested over a 2-week period. At the end of the 2-weeks the animals were sacrificed, the grafts were then pressure fixed and harvested. Morphometric analysis of the histologic specimen demonstrated that cell seeding improved patency (76% versus 52%, p=0.036 chi square analysis) and inhibited the formation of TEVG stenosis as measured by comparison of luminal diameter between groups (0.54 mm±0.27 mm s.d. versus 0.37 mm±0.28 mm s.d., p=0.031 unpaired T-test) (Table 2, FIG. 1A). Further analysis and comparison of the seeded versus unseeded scaffolds demonstrated significant difference in the degree of macrophage infiltration in the seeded versus unseeded scaffolds (421 cells/HPF ±93cells/HPF s.d. versus 555 cells/HPF ±89 cells/HPF s.d., p=0.029 unpaired T-test) implanted in the CB57/BL6 mice at the 2-week time point (FIG. 1B). Additionally we analyzed and compared the macrophage infiltration between patent and stenosed TEVG and found that stenotic TEVG had a higher degree of macrophage infiltration (374 cells/HPF ±29 cells/HPF s.d.versus 569 cells/HPF ±62 cells/HPF s.d., p=0.0001 unpaired T-test) (FIG. 1C). These findings indicate that cell seeding improves TEVG patency by inhibiting the formation of TEVG stenosis. In addition these data show a correlation between the degree of macrophage infiltration and the formation of stenosis in TEVG suggesting that cell seeding may inhibit the formation of TEVG stenosis by altering the host inflammatory response.

TABLE 2

Graft patency at 2 weeks (Total N = 50)

|  | Patent | Occluded |
| --- | --- | --- |
| Seeded (N = 25) | 19 (76%) | 6 (24%) |
| Unseeded (N = 25) | 13 (52%) | 12 (48%) |

Fate of Seeded Cells

It was previously shown that cells seeded onto the scaffold disappear and are rapidly replaced by host-derived macrophages (Roh, J. D., et al. Proc. Natl. Acad. 107:4669-74 (2010)). These findings were not consistent with the classic tissue engineering paradigm in which the seeded cells were viewed as the building blocks of neotissue (Vacanti, J. P. & Langer, R. Lancet, 354 Suppl 1:S132-4 (1999); Langer, R. & Vacanti, J. P. Science, 260:920-6 (1993)). These finding were based on the use of a chimera in which TEVG constructed by seeding human bone marrow-derived mononuclear cells were implanted in SCID-beige recipient mice (Roh, J. D., et al. Proc. Natl. Acad. 107:4669-74 (2010)). The fate of the seeded cells was then determined using species-specific immunohistochemical markers and validated using human specific molecular probes (Roh, J. D., et al. Proc. Natl. Acad. 107:4669-74 (2010)).

Figure 2A:
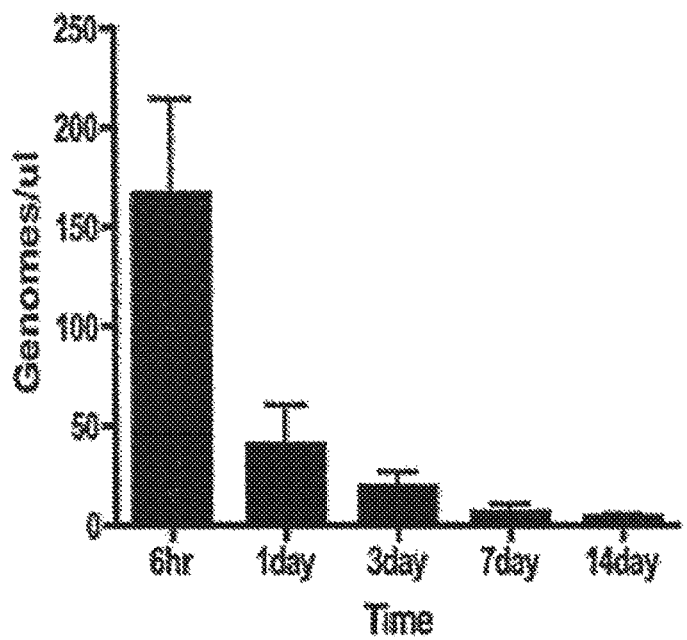
FIG. 2A is a bar graph showing quantification of GFP (genomes/µl) in TEVG seeded with GFP positive cells, implanted in a GFP negative host, and harvested 6 hrs (bar 1), 1 day (bar 2), 3 days (bar 3), 7 days (bar 4), or 14 days (bar 5) after implantation.
Figure 2B:
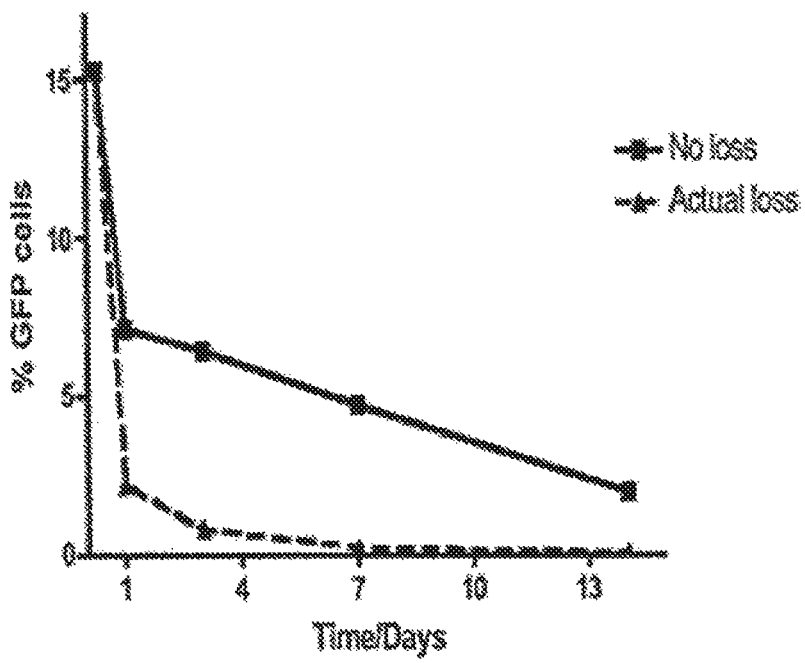
FIG. 2B is a graph demonstrating GFP quantification (% GFP cells) in TEVG with (-■-) or without loss (-▲-).

In light of data suggesting a possible role of inflammatory cells in vascular neotissue formation and the development of TEVG stenosis, the fate of the seeded cells was investigated using an immune competent animal model. TEVGs (N=30) constructed by seeding the scaffold with GFP-labeled syngeneic bone morrow-derived mononuclear cells were implanted and then the scaffolds harvested over a 2-week time course and the percentage of GFP DNA quantified at various time points. Once again, it was demonstrated that the seeded cells disappear and were rapidly replaced by host-derived cells (FIGS. 2A and 2B). To demonstrate that this was not simply a dilutional effect due to increased cell density secondary to the infiltrating host inflammatory cells, the GFP data was normalized to cell density. These findings confirm that the seeded cells disappeared and were replaced by host-derived cells.

Mechanisms of Neovessel Formation

Based on the finding that there was a positive correlation between the degree of macrophage infiltration and the formation of TEVG stenosis, the role of the macrophage infiltration on neovessel formation was investigated. TEVG was implanted as IVC interposition grafts into CB57/BL6 mice, which had been macrophage depleted using clodronate liposomes. Pretreatment with the clodronate liposomes had a profound effect on both animal weight and perioperative mortality with approximately 67% of the mice treated with 600 µl of clodronate and 33% of the mice treated with 200 µl of clodronate liposomes not surviving surgery compared to 0% mortality in the sham treated group. None of the perioperative deaths were graft related.

Figure 3A:
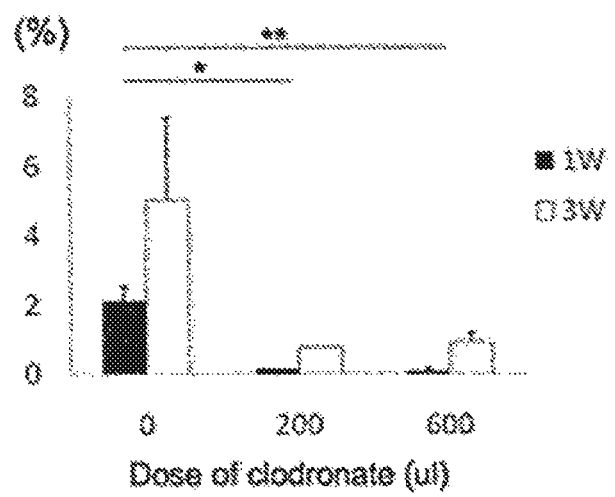
FIGS. 3A to 3C are bar graphs showing circulating CD115 monocytes (%) (FIG. 3A), luminal diameter (mm) (FIG. 3B), or macrophage infiltration (cell/HPF (x400))
Figure 3B:
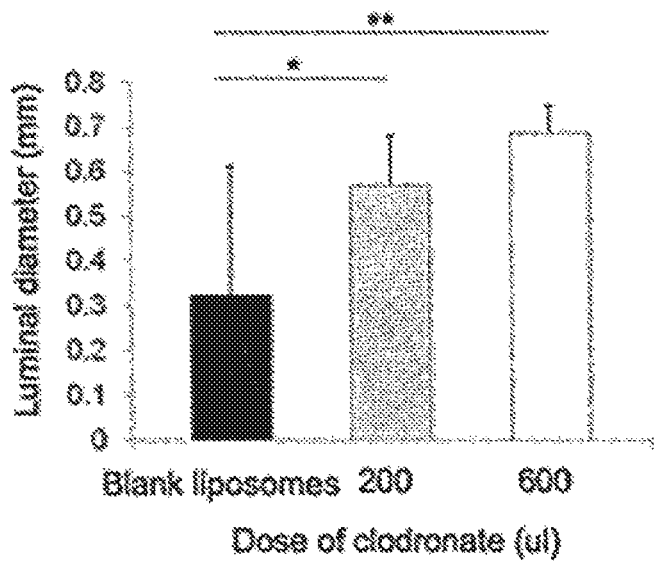
Figure 3C:
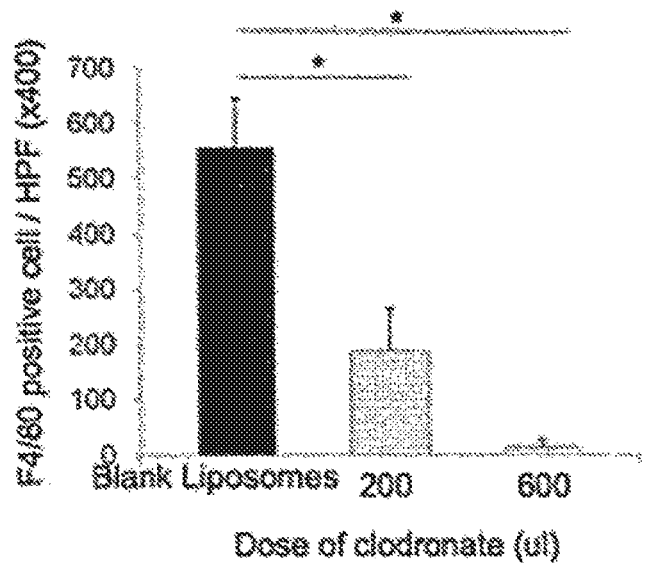
Figure 4A:
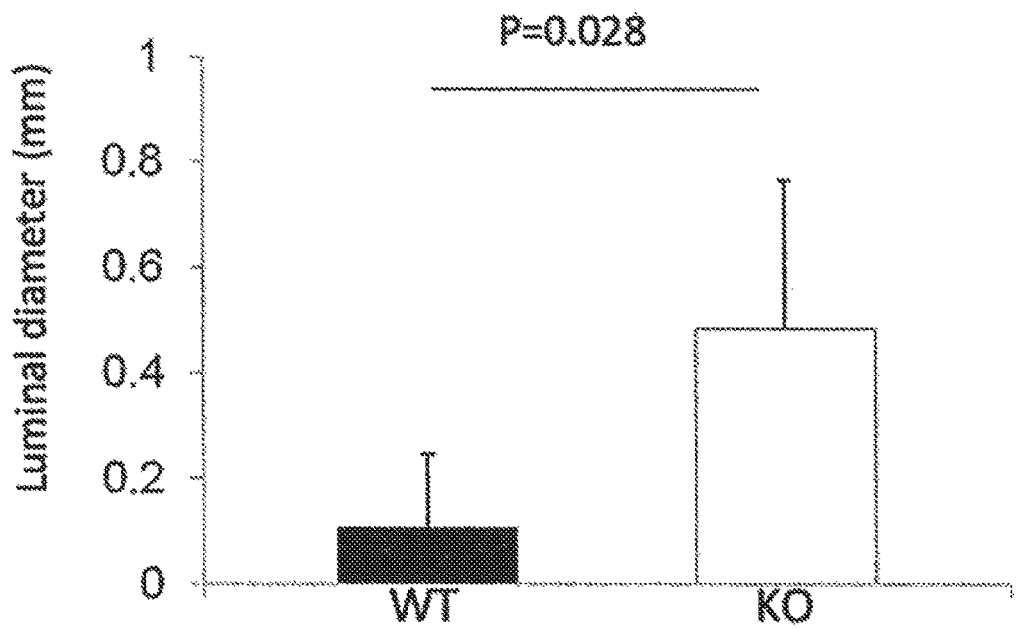
FIGS. 4A and 4B are bar graphs showing luminal diameter (mm) (FIG. 4A) or macrophage infiltration (cell/HPF (x400)) (FIG. 4B) TEVG implanted in either wild type (column 1) or MCP-1 null (KO) (column 2) mice.
Figure 4B:
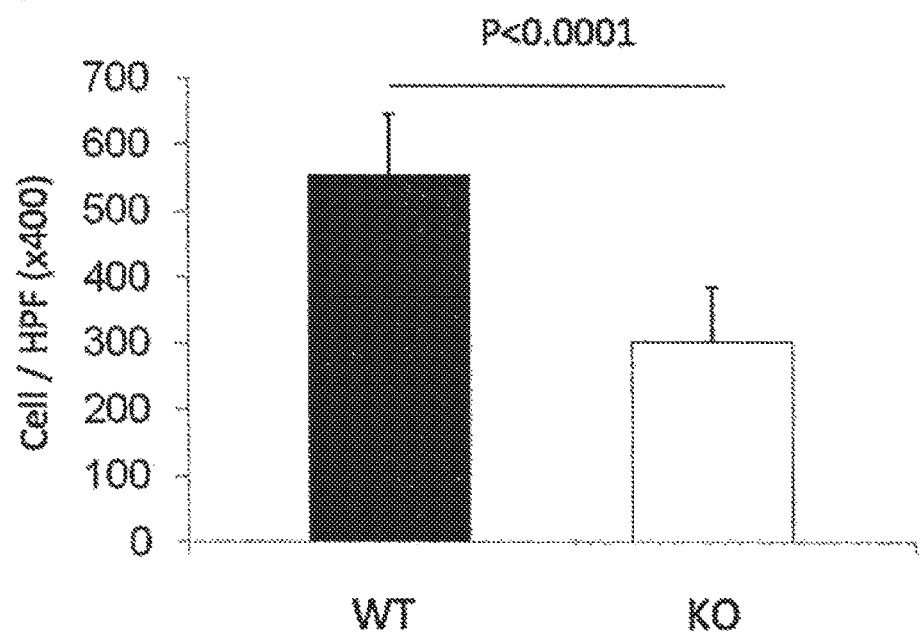

TEVGs were implanted into mice that had been macrophage depleted with either 200 µl of clodronate liposomes per day (N=6 survivors) or 600 µl of clodronate liposomes per day (N=4/survivors) and the results were compared to sham treated (blank liposomes) mice (N=8 survivors) (FIG. 3A). At the end of the two-week period the animals were sacrificed, the TEVG pressure fixed, and harvested. Morphometric examination of the histological specimen demonstrated there was increased internal diameter between the macrophage depleted and non-depleted groups (0.69 mm±0.06 mm s.d. versus 0.57 mm±0.11 mm s.d. versus 0.32 mm±0.29 mm s.d.) (FIG. 3B). Quantification of the number of macrophages in each group demonstrated a dose related reduction in the degree of macrophage infiltration and that the reduction in macrophage density correlated with decreased stenosis and increased luminal diameter (FIG. 3C). These results suggest a critical role of host-derived macrophages in neovessel formation and the formation of TEVG stenosis.

Figure 5A:
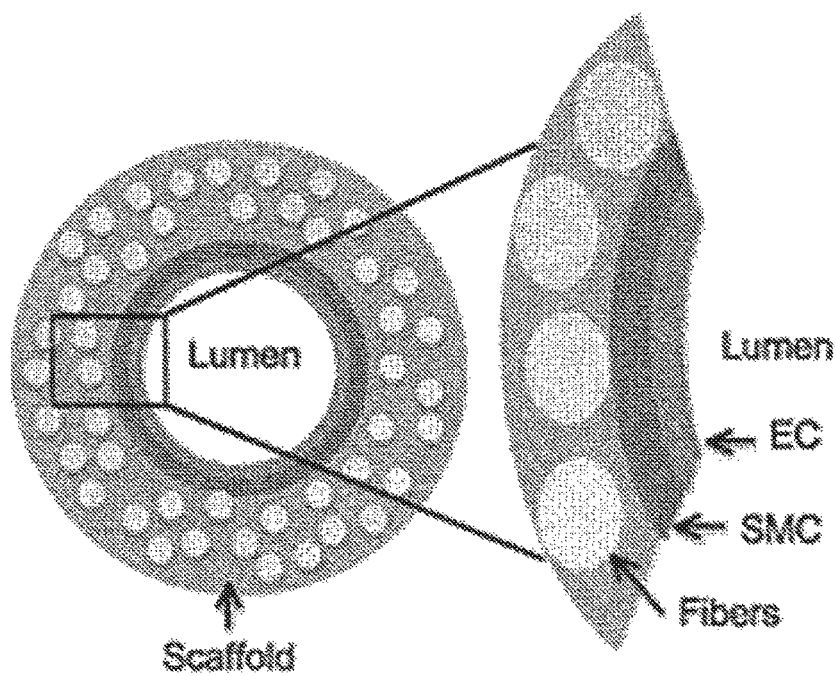
FIG. 5A is a schematic illustrating observations from confocal microscopic images of TEVG implanted into female host that had undergone transplantation with male bone marrow harvested 6 months after implantation.

Based on the discovery that the seeded cells inhibit stenosis but rapidly disappear from the TEVG after implantation, it was hypothesized that the seeded cells inhibited stenosis by altering the recruitment of monocytes to the scaffold via a paracrine mechanism. Monocyte chemoattractant protein-1 (MCP-1) could be an important mediator in this process. Therefore the role of MCP-1 was investigated by implanting unseeded tissue engineered vascular grafts into either MCP-1 knockout mice (N=5) or wild type (CB57/BL6) mice (N=5) over a 2-week period. After 2 weeks the animals were sacrificed, the TEVG pressure fixed, and harvested. Morphometric analysis of the histologic specimen demonstrated improved graft patency (80% versus 0%, p=0.016 chi square) due to decreased stenosis as demonstrated by increased luminal diameter in the MCP-1 null versus the wild type mice (0.48 mm±0.28 mm s.d. versus 0.11 mm±0.14 mm s.d., p=0.028 unpaired T-test) (FIG. 5A). Quantitative evaluation of the degree of macrophage infiltration demonstrated increase macrophage infiltration in the TEVG implanted in the wild type versus MCP-1 null mice demonstrated increased macrophage infiltration in the TEVG implanted in the wild type mice (591 cells/ HPF±74 cells/HPF s.d. versus 301 cells/HPF±84 cells/HPF s.d., p=0.00002 unpaired T-test) suggesting that MCP-1 plays a critical role in TEVG stenosis and highlighting the importance of the host-derived macrophage in the formation of TEVG stenosis.

Source of Vascular Neotissue (Blood Vessel Regeneration)

Figure 5B:
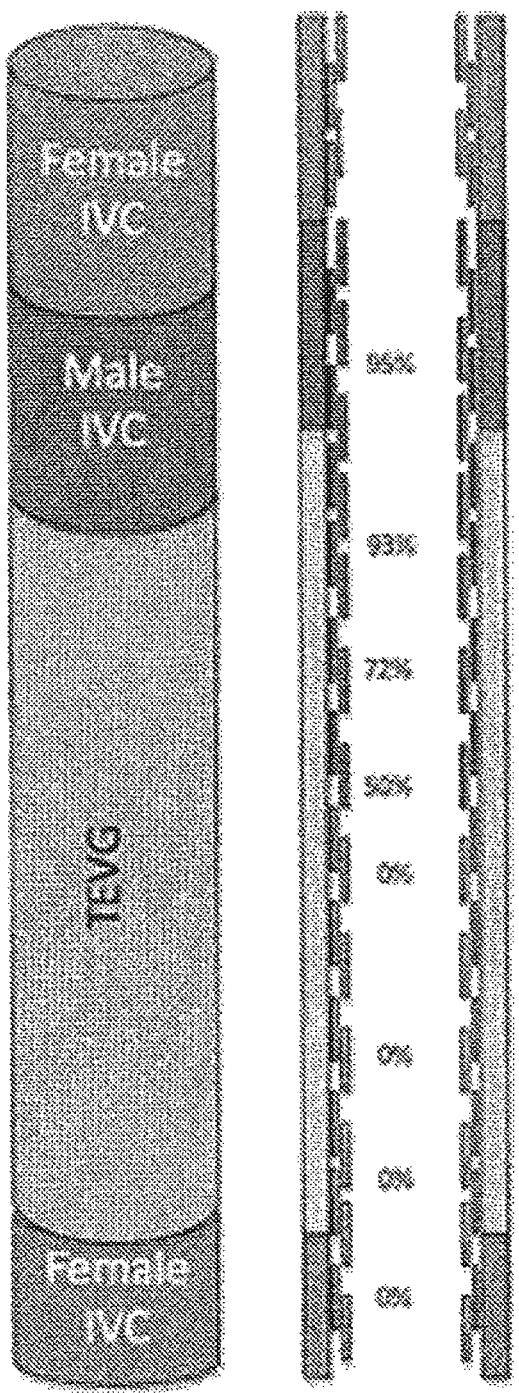
FIG. 5B is a schematic of a composite TEVG creating by anastomosing a male inferior vena cava (IVC) with a TEVG and implanting into a female host showing the male IVC, proximal TEVG, and distal TEVG.

A series of experiments were designed to determine the source of the cells that contribute to the vascular neotissue. To determine the source of the infiltrating macrophages TEVGs were implanted into female mice which had undergone bone marrow transplantation with syngeneic male bone marrow and then the TEVGs (N=52) were harvested at various times over a six month period; the specimens were analyzed using FISH for the Y chromosome and a variety of other cellular markers for macrophages (F4-80), smooth muscle cells (calponin), and endothelial cells (vWF). These experiments demonstrated that the macrophages that infiltrated the scaffold were of male origin and therefore were derived from the bone marrow. However there was no evidence of co-localization of either smooth muscle cell markers or endothelial cell markers with the Y chromosome marker suggesting that the bone marrow was not the ultimate source of the vascular neotissue (FIG. 5A). To determine if the endothelial cells or smooth muscle cells derived from the neighboring blood vessel, an experiment was performed using a composite vascular graft created by anastomising a segment of syngeneic male IVC with a TEVG. The composite vascular grafts (N=8) were then implanted into female hosts and harvested over a six-month period. The composite graft and neighboring IVC were then evaluated using FISH for the Y-chromosome and analyzed. Both the endothelial cells and smooth muscle cells contained the Y-chromosome. Additionally the density of Y-chromosome positive cells was greater closer to the implanted male IVC suggesting that neovessel formation arises from in-growth of endothelial and smooth muscle cells from the neighboring blood vessel resulting in blood vessel regeneration (FIG. 5B).

We claim:

1. A method for maintaining patency in an implanted cell-free biodegradable polymeric vascular graft comprising administering to a subject between three days prior to vascular graft implantation and two weeks following vascular graft implantation, a macrophage inhibitor selected from the group consisting of antibodies, antibody fragments and antibody conjugates inhibiting macrophages, bisphosphonates, and anti-folate inhibitors,
wherein the macrophage inhibitor is in an amount effective to reduce the recruitment of host monocytes into the vascular graft and to promote attachment and proliferation of endothelial and smooth muscle cells from adjacent vessels onto the inner surface of the graft relative to an untreated control and promote neotissue formation with reduced stenosis, thrombus or aneurysm formation at the site of the implanted cell-free polymeric vascular graft, and
wherein the polymeric vascular graft optionally includes an active agent selected from the group consisting of anti-thrombogenic agents, anti-inflammatory agents, anesthetic agents, anti-coagulants, cholesterol-lowering agents, vasodilating agents, and agents which interfere with endogenous vasoactive mechanisms; wherein patency of said graft is increased compared to the same graft which has been seeded with cells prior to implantation.

2. The method of claim 1, wherein the macrophage inhibitor is a bisphosphonate selected from the group consisting of alendronate, clodronate, EB-1053, etidronate, ibandronate, incadronate, neridronate, olpadronate, pamidronate, risedronate, tiludronate, YH 529, and zoledronate.

3. The method of claim 1, wherein the macrophage inhibitor is an anti-folate inhibitor selected from the group consisting of methotrexate, trimethoprim, pyrimethamine, pemetrexed, raltitrexed, and pralatrexate.

4. The method of claim 1, wherein the macrophage inhibitor is an antibody, antibody fragments or antibody conjugates inhibiting macrophages reactive with CD14, IB4, OKM1, OKM9, or OKM10.

5. The method of claim 1, wherein the macrophage inhibitor is encapsulated in the form of liposomes, microspheres, nanospheres, microparticles and/or microcapsules that are seeded into, onto or dispersed within the vascular graft.

6. The method of claim 1, wherein the vascular graft includes an active agent selected from the group consisting of anti-thrombogenic agents, anti-inflammatory agents, anesthetic agents, anti-coagulants, cholesterol-lowering agents, vasodilating agents, and agents which interfere with endogenous vasoactive mechanisms.

7. The method of claim 1, wherein the macrophage inhibitor is in a controlled release formulation.

8. The method of claim 1, wherein the polymers forming the polymeric vascular graft are biodegradable and the polymers are formed into a fiber-containing woven or nonwoven mesh.

* * * * *

UNITED STATES PATENT AND TRADEMARK OFFICE
CERTIFICATE OF CORRECTION

PATENT NO. : 10,300,082 B2
APPLICATION NO. : 15/097716
DATED : May 28, 2019
INVENTOR(S) : Christopher K. Breuer and Tarek Fahmy Page 1 of 1

It is certified that error appears in the above-identified patent and that said Letters Patent is hereby corrected as shown below:

In the Specification

Column 1, Lines 16-19, replace "This invention was made with government support under Agreement No. HL098228 awarded by the National Institutes of Health. The government has certain rights in the invention." with "This invention was made with government support under HL083980 and HL098228 awarded by the National Institutes of Health. The government has certain rights in the invention."

Signed and Sealed this
Twenty-sixth Day of May, 2020

Andrei Iancu
*Director of the United States Patent and Trademark Office*